(12) United States Patent
Larma et al.

(10) Patent No.: US 7,045,147 B1
(45) Date of Patent: May 16, 2006

(54) CONTROLLED RELEASE PERORAL COMPOSITIONS OF LEVOSIMENDAN

(75) Inventors: Iikka Larma, Springfield, NJ (US); Maarit Bäckman, Helsinki (FI); Saila Antila, Helsinki (FI); Lasse Lehtonen, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/673,794

(22) PCT Filed: Apr. 23, 1999

(86) PCT No.: PCT/FI99/00329

§ 371 (c)(1),
(2), (4) Date: Dec. 20, 2000

(87) PCT Pub. No.: WO99/55305

PCT Pub. Date: Nov. 4, 1999

(30) Foreign Application Priority Data

Apr. 23, 1998 (FI) ................................................ 980901

(51) Int. Cl.
*A61K 9/14* (2006.01)

(52) U.S. Cl. .................. 424/489; 424/464; 424/451
(58) Field of Classification Search ................ 424/400, 424/451, 464, 489, 468, 493, 480, 449, 434, 424/484; 514/54
See application file for complete search history.

(56) References Cited

U.S. PATENT DOCUMENTS 4,716,042 A 12/1987 Blank
5,213,811 A * 5/1993 Frisbee et al. .............. 424/451
6,531,458 B1 * 3/2003 Larma et al. ................. 514/54

FOREIGN PATENT DOCUMENTS

| EP | 0091767 A2 | * 10/1983 |
| EP | 0 091 767 | 10/1983 |
| EP | 0 383 449 | 8/1990 |
| WO | WO 92/12135 | 7/1992 |
| WO | WO 93/21921 | 11/1993 |
| WO | WO 9321921 A1 | * 11/1993 |
| WO | WO 98/01111 | 1/1998 |
| WO | WO 99/16443 | 4/1999 |

OTHER PUBLICATIONS

Sandell et al., "Pharmacokinetics of Levosimendan in Healthy Volunteers and Patients with Congestive Heart Failure," J. Cardiovascular Pharmacology, vol. 26, Suppl. 1, pp. S57–S62 (1995).

Sundberg et al., "Hemodynamic and Neurohumoral Effects of Levosimendan, a New Calcium Sensitizer, at Rest and During Exercise in Healthy Men," American Journal of Cardiology, vol. 75, pp. 1061–1066 (1995).

* cited by examiner

*Primary Examiner*—Thurman K. Page
*Assistant Examiner*—Robert M. Joynes
(74) *Attorney, Agent, or Firm*—Finnegan, Henderson, Farabow, Garrett & Dunner, LLP

(57) ABSTRACT

The invention relates to peroral pharmaceutical compositions which release levosimendan in a controlled fashion with reduced occurrence of undesired effects. Levosimendan, or (−)-[[4-(1,4,5,6-tetrahydro-4-methyl-6-oxo-3-pyridazinyl)phenyl]-hydrazono]propanedinitrile, is useful in the treatment of congestive heart failure.

17 Claims, 3 Drawing Sheets

CONTROLLED RELEASE PERORAL COMPOSITIONS OF LEVOSIMENDAN

This application is a national stage filing of PCT International Application No. PCT/FI99/00329, filed on Apr. 23, 1999, which published in English.

TECHNICAL FIELD

The present invention relates to peroral pharmaceutical compositions which release levosimendan in a controlled fashion with reduced occurrence of undesired effects. Levosimendan, or (−)-[[4-(1,4,5,6-tetrahydro-4-methyl-6-oxo-3-pyridazinyl)phenyl]hydrazono]propanedinitrile, is useful in the treatment of congestive heart failure.

BACKGROUND OF THE INVENTION

Levosimendan, which is the (−)-enantiomer of [[4-(1,4,5,6-tetrahydro-4-methyl-6-oxo-3-pyridazinyl)phenyl]hydrazono]propanedinitrile, and the method for its preparation is described in EP 565546 B1. Levosimendan is potent in the treatment of heart failure and has significant calcium dependent binding to troponin. Levosimendan is represented by the formula:

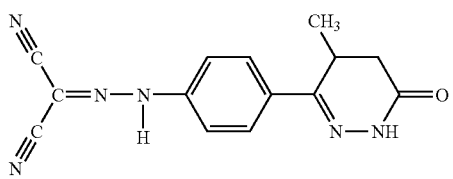

I

The hemodynamic effects of levosimendan in man are described in Sundberg, S. et al., Am. J. Cardiol., 1995; 75: 1061–1066. Pharmacokinetics of levosimendan in man after i.v. and oral dosing is described in Sandell, E. -P. et al., J. Cardiovasc. Pharmacol., 26(Suppl. I), S57–S62, 1995. The use of levosimendan in the treatment of myocardial ischemia is described in WO 93/21921. Clinical studies have confirmed the beneficial effects of levosimendan in heart failure patients.

Oral administration of levosimendan has proved to be difficult, especially when the aim is a therapeutical effect over an extended period of time. Firstly, the elimination half-life of levosimendan in human is short, about 1 h. Therefore, using conventional immediate release oral formulations levosimendan should be administered frequently during the day. Secondly, the gastrointestinal absorption of levosimendan is rapid. Therefore, using immediate release oral formulations high peak plasma concentrations of levosimendan are reached rapidly and abruptly, typically within 1 hour. High plasma concentrations of levosimendan tend to increase heart rate which is an undesired effect in heart failure patients.

Long-acting peroral compositions provide many advantages over conventional peroral rapid release compositions. Such advantages include smaller variation of drug concentrations in plasma and, as a result, steady therapeutic response, reduced frequency of administration and reduction of side effects. Typically long-acting compositions are prepared by mixing the drug, a release controlling agent and possible excipients, and pressing the mixture into matrix tablets. Typical long-acting compositions release drug in the upper as well as in the lower gastrointestinal tract.

Attempts to administer levosimendan in conventional long-acting preparations have been disappointing. Undesired effects such as severe headache, palpitation and increased heart rate are frequently observed when levosimendan is administered in long-acting preparations which are conventionally used in the art to obtain a therapeutical effect over an extended period of time. Therefore there is a need for new methods and compositions for administering levosimendan orally, in particular for methods and compositions which provide a therapeutical effect of levosimendan over an extended period of time and which avoid the drawbacks associated with the conventional long-acting preparations of levosimendan.

SUMMARY OF THE INVENTION

It has been found that levosimendan is susceptible to metabolization in the lower gastrointestinal tract, in particular in the large intestine, by the intestinal bacteria. Such metabolic route results ultimately in the formation of an active first-pass metabolite, (R)-N-[4-(1,4,5,6-tetrahydro-4-methyl-6-oxo-3-pyridazinyl)phenyl]acetamide (II) having elimination half-life substantially longer than that of levosimendan. The accumulation of the active metabolite has been found to be the cause of the undesired effects associated with the long-acting levosimendan preparations. The discovery of the active metabolite and its formation route makes it now possible to design controlled release preparations which show a reduced occurrence of undesired effects and which are well suited for the treatment of heart failure patients.

Therefore the object of the present invention is to provide peroral compositions, in particular compositions which provide a therapeutical effect over an extended period of time, from which levosimendan is released steadily and, preferably, substantially completely before it reaches the lower part of the gastrointestinal tract, particularly the large intestine, so that the formation of the active metabolite remains at low level. Thereby, the concentration of the active metabolite in the plasma of the patient remains at sufficiently low level so that the undesired effects caused by the accumulation of the active metabolite are avoided while a therapeutical effect over an extended period of time is obtained.

DETAILED DESCRIPTION

Figure 1:
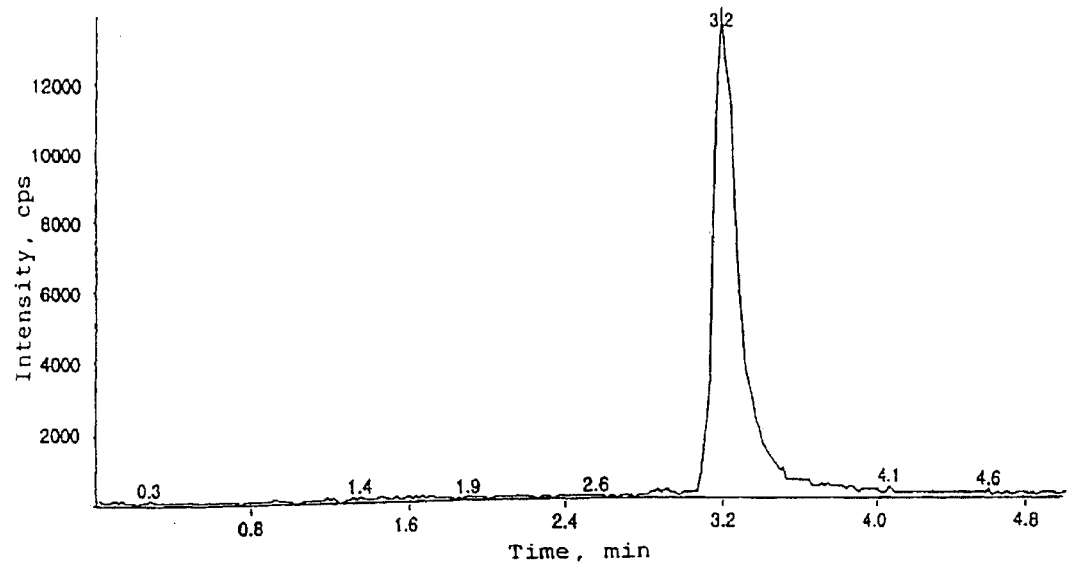
FIG. 1 shows a calibration sample for the active metabolite (II) from a volunteer as determined by liquid chromatography-tandem mass spectrometry.

The present invention provides an improved oral delivery system for levosimendan compared to conventional immediate release and long-acting preparations. The advantages include:

lower peak plasma levels of levosimendan which hence reduce the occurrence of the undesired effects of high levosimendan levels such as increased heart rate, reduced frequency of administration, and reduced accumulation of the active metabolite (II) which mean higher tolerability of the drug, i.e. less undesired effects caused by the active metabolite, such as severe headache, palpitation and increased heart rate.

The plasma level of metabolite (II) correlates well with the occurrence of undesired effects such as severe headache, palpitation and increased heart rate. In the optimal levosimendan treatment of heart failure patients the steady-state plasma level of metabolite (II) should be less than 20 ng/ml, preferably less than 10 ng/ml.

The advantages are provided according to the invention by a controlled release composition comprising a) a therapeutically effective amount of levosimendan and b) a drug release controlling component for providing the release of levosimendan in a patient over an extended period of time and a steady-state plasma level for metabolite (II) of less than 20 ng/ml, preferably less than 10 ng/ml.

The term "an extended period of time" means above at least one hour, preferably at least two hours, after administration. The steady-state plasma level of metabolite (II) as defined above refers to an average among a group of patients.

Preferably the drug release controlling component allow levosimendan to be released substantially completely before the composition reaches the large intestine.

The term "drug release controlling component" relates generally to different technologies that can be applied for controlling and extending the release of levosimendan according to the invention. Such technologies include matrix formulations (e.g. matrix tablets, granules or pellets) or coated formulations (e.g. coated tablets, granules or pellets, or microcapsules). The drug release controlling components such as coating and matrix materials, and the methods for the preparation of matrix and coated formulations are well know in the art. The choice of the materials and the amounts used depends on the desired release pattern and is routine to one skilled in the art. Any release controlling materials, e.g. matrix or coating materials, or their combinations which are suitable for obtaining the release pattern of the invention can be used as a drug release controlling component. Typical release controlling components useful in the invention include, but are not limited to, hydrophilic gel forming polymers such as hydroxypropylmethyl cellulose, hydroxypropyl cellulose, carboxymethyl celluloses, alginic acid or a mixture thereof; vegetable fats and oils including vegetable solid oils such as hydrogenated soybean oil, hardened castor oil or castor seed oil (sold under trade name Cutina HR), cotton seed oil (sold under the trade names Sterotex or Lubritab) or a mixture thereof; fatty acid esters such as triglycerides of saturated fatty acids or their mixtures e.g. glyceryl tristearates, glyceryl tripalmitates, glyceryl trimyristates, glyceryl tribehenates (sold under the trade name Compritol) and glyceryl palmitostearic acid ester.

According to the invention it is also possible to use formulations which are designed to have extended residence time in the upper gastrointestinal tract, e.g. the stomach. This reduces the risk of levosimendan metabolization in the large intestine and the subsequent formation of the active metabolite (II). Such compositions, e.g. floating or buoyant formulations, have the advantage that the total release time of the drug can be designed to be substantially longer, since it takes substantially longer time before the composition reaches the lower part of the gastrointenstinal tract. Compositions having extended residence time in the stomach are described e.g. in U.S. Pat. Nos. 4,126,672, 4,814,178, 4,777,033, 5,232,704 and EP 539059.

Thus, any controlled/extended release composition of levosimendan, which gives a steady-state plasma level for metabolite (II) of less than 20 ng/ml, preferably less than 10 ng/ml, can be used according to the present invention.

The steady-state plasma level for metabolite (II) can be measured for any composition by administering the composition of levosimendan to a volunteer or group of volunteers once or several times a day for several days until a steady state level of (II) is reached. The plasma levels of the active metabolite (II) can then be measured according to the procedure described in detail in Example 2.

One aspect of the invention is a controlled release composition of levosimendan for oral administration which is characterized by its in vitro dissolution pattern.

In particular, the invention relates to a controlled release composition for oral administration comprising a) a therapeutically effective amount of levosimendan and b) a drug release controlling component for providing the release of levosimendan over an extended period of time, which composition is able to show a total in vitro dissolution time, determined according to the USP XXII basket assembly method in phosphate buffer pH 5.8 (at 50 or 100 rpm), substantially between 1 and 4 hours, for at least 90 percent of the content of levosimendan.

More preferably, the composition of the invention shows a total in vitro dissolution time substantially between 1 and 3 hours, for at least 90 percent of the content of levosimendan.

The drug release controlling component or components can be chosen as described above. Again, typical release controlling components include, but are not limited to, hydrophilic gel forming polymers such as hydroxypropylmethyl cellulose, hydroxypropyl cellulose, carboxymethyl celluloses, alginic acid or a mixture thereof; vegetable fats or oils or fatty acid esters such as hydrogenated soybean oil, hardened castor oil or glyceryl palmitostearate.

The method of determining the in vitro dissolution pattern of the compositions of the invention is described in Example 3.

The composition of the invention can be e.g. in the form of a tablet, capsule, granulates or powder.

A particularly preferred embodiment of the invention is obtained by combining a rapid release portion comprising levosimendan optionally together with an excipient with a controlled release portion comprising levosimendan and a drug release controlling component. The drug release controlling component can be chosen as described above, but is preferably a hydrophilic gel forming polymer. Particularly preferred is a composition comprising (a) a rapid release portion in the form of a powder comprising levosimendan together with at least one excipient, and (b) a controlled release portion in the form of granulates comprising levosimendan and a release controlling hydrophilic gel forming polymer. The rapid release portion in the form of a powder and the controlled release portion in the form of granulates are preferably in a freely flowing mixture which can be filled in a capsule, such as a gelatine capsule or a HPMC capsule.

The particularly preferred composition of the invention comprises 0.05–20%, preferably 0.1–10%, more preferably 0.2–3%, per weight of the composition, of levosimendan. The drug dose is divided between the rapid release and the controlled release portions. Generally about 25–75%, preferably about 30–70%, more preferably about 40–60% per weight of the drug is in the controlled release portion.

In general, the daily dosage of levosimendan in man in oral administration is from about 0.1 to 20 mg, typically from about 0.5 to 10 mg, in one daily dose or divided into several doses per day. The dosage depends e.g. on the age, body weight and condition of the patient. The composition of the preferred embodiment comprises from about 0.1 to 5 mg, typically from about 0.2 to 2 mg, of levosimendan divided between the rapid release and the controlled release portions. Preferred peak plasma levels of levosimendan in steady state for the treatment of congestive heart failure are within the range of from about 1 to about 100 ng/ml, more preferably from about 5 to about 60 ng/ml, and most preferably from about 10 to about 50 ng/ml.

A suitable excipient in the rapid release portion is a filler such as microcrystalline cellulose or lactose. Microcrystalline cellulose is a preferred excipient and is available in various grades such as Avicel PH101, Avicel PH102 or Avicel PH200. The amount of the excipients in the rapid release portion is about 20–70%, preferably about 30–60%, per weight of the composition. A suitable lubricant such as stearic acid or magnesium stearate can be added to the rapid release portion. Stearic acid is the preferred lubricant.

Release controlling hydrophilic gel forming polymers include, but are not limited to hydroxypropylmethyl cellulose, hydroxypropyl cellulose, carboxymethyl celluloses, alginic acid or a mixture thereof. Preferred is a mixture of alginic acid with another hydrophilic gel forming polymer, in particular a mixture of alginic acid and hydroxypropylmethyl cellulose. Hydroxypropylmethyl cellulose is commercially available in various types, e.g. Methocel K100 (m.w. 26,000 g/mol), Methocel K4M (m.w. 86,000 g/mol, Methocel K15M (m.w. 120,000 g/mol) and Methocel K100M. The viscosity of these grades in 2% water solution (20° C.) is 100 cP, 4000 cP, 15000 cP and 100000 cP, respectively. Hydroxypropylmethyl cellulose with viscosity between 50–2000 cP is preferred. Methocel K100 is the preferred grade of hydroxypropylmethyl cellulose.

A suitable lubricant such as stearic acid or magnesium stearate can be added to the controlled release portion. Stearic acid is the preferred lubricant.

The amount of the hydrophilic gel forming polymer in the particularly preferred embodiment of the invention is about 20–80%, preferably 30–70%, per weight of the composition. Preferably the hydrophilic gel forming polymer is a mixture of alginic acid and hydroxypropylmethyl cellulose. Suitably the amount of alginic acid is from about 10 to 50%, preferably from about 20 to 40%, per weight of the total hydrophilic gel forming polymer.

The amount of the rapid release portion is in the particularly preferred embodiment of the invention from about 20 to 80%, preferably from about 30 to 70%, more preferably from about 40 to 60%, per weight of the composition. The amount of the lubricant, if present, is from about 0.3 to 10%, more preferably from about 0.5 to 5%, per weight of the composition.

Another preferred embodiment of the invention is obtained by mixing the drug release controlling component, levosimendan and excipients e.g. all in powder form, and filling the mixture into a capsule, such as a gelatine capsule or a HPMC capsule. Drug release controlling component can be chosen as described above. Preferably the drug release controlling component is a hydrophilic gel forming polymer, which in this embodiment is used in an amount from about 10 to 70%, preferably from about 15 to 60%, most preferably from about 20 to 40%, per weight of the composition. Release controlling hydrophilic gel forming polymers include, but are not limited to hydroxypropylmethyl cellulose, hydroxypropyl cellulose, carboxymethyl celluloses, alginic acid or a mixture thereof. The most preferred drug release controlling component is hydroxypropylmethyl cellulose, and particularly hydroxypropylmethyl cellulose with viscosity between 50–2000 cP such as Methocel K100, and alginic acid or a mixture thereof. The amount of excipient (e.g. microcrystalline cellulose or lactose) is suitably used in this embodiment in an amount from about 30 to 90%, preferably from about 40 to 80%, most preferably from about 50 to 70% per weight of the composition. Levosimendan is used in an amount as described for the previous preferred embodiment.

Yet another preferred embodiment of the invention is in a form of a matrix tablet which is obtained by mixing the drug release controlling component, levosimendan and excipients, such as microcrystalline cellulose, lactose and/or stearic acid, and compressing the mixture into matrix tablets with a suitable tablet machine. Again, drug release controlling component can be chosen as described above. Preferably the drug release controlling component is a hydrophilic gel forming polymer or a vegetable fat or oil or a fatty acid ester as defined above. In this embodiment the drug release controlling component is used in an amount from about 0.5 to 60% per weight of the composition, and the amount of excipient (e.g. microcrystalline cellulose) is suitably used in an amount from about 30 to 99%, per weight of the composition. If the drug release controlling component is a hydrophilic gel forming polymer, e.g. hydroxypropylmethyl cellulose, and preferably hydroxypropylmethyl cellulose with viscosity between 50–2000 cP such as Methocel K100, alginic acid or a mixture thereof, the drug release controlling component is used in an amount from about 5 to 60%, preferably from about 10 to 50%, most preferably from about 15 to 40%, per weight of the composition, and the amount of excipient (e.g. microcrystalline cellulose) is suitably used in an amount from about 30 to 95%, preferably from about 50 to 90%, most preferably from about 60 to 85%, per weight of the composition. If the drug release controlling component is a vegetable fat or oil or a fatty acid ester, e.g. hydrogenated soybean oil, hardened castor oil or glyceryl palmitostearate, the drug release controlling component is used in an amount from about 0.5 to 30%, preferably from about 2 to 20%, most preferably from about 3 to 15%, per weight of the composition, and the amount of excipient (e.g. microcrystalline cellulose) is suitably used in an amount from about 70 to 99%, preferably from about 80 to 98%, most preferably from about 85 to 97%, per weight of the composition. Levosimendan is used in an amount as described for the previous preferred embodiment.

The following examples are meant to further illustrate the invention without limitation.

EXAMPLE 1

Formulation Examples

| Formulation 1. | | |
|---|---|---|
| Granule portion: | Levosimendan | 1.0 mg |
| | Alginic acid | 18.0 mg |
| | Methocel K100LV | 37.0 mg |
| | Stearic acid | 0.6 mg |
| Powder portion: | Levosimendan | 1.0 mg |
| | Avicel PH101 | 84.0 mg |
| | Stearic acid | 1.5 mg |
| Formulation 2. | | |
| Granule portion: | Levosimendan | 1.0 mg |
| | Alginic acid | 23.0 mg |
| | Methocel K100LV | 46.0 mg |
| | Stearic acid | — |
| Powder portion: | Levosimendan | 1.0 mg |
| | Avicel PH101 | 69.5 mg |
| | Stearic acid | 1.5 mg |

-continued

| Formulation 3. | | |
|---|---|---|
| Granule portion: | Levosimendan | 1.0 mg |
| | Alginic acid | 28.0 mg |
| | Methocel K100LV | 56.0 mg |
| | Stearic acid | 0.9 mg |
| Powder portion: | Levosimendan | 1.0 mg |
| | Avicel PH101 | 56.0 mg |
| | Stearic acid | 1.5 mg |
| Formulation 4. | | |
| Granule portion: | Levosimendan | 1.0 mg |
| | Alginic acid | 33.0 mg |
| | Methocel K100LV | 66.0 mg |
| | Stearic acid | 0.6 mg |
| Powder portion: | Levosimendan | 1.0 mg |
| | Avicel PH101 | 43.0 mg |
| | Stearic acid | 1.5 mg |

In the above examples the material for the granule portion was sieved and mixed until homogenous in a suitable mixer such as Turbula mixer or Zanchetta container mixer. The powder blend was sieved through 0.6 mm screen. The mass was dry granulated by slugging (compressed using a tabletting machine). In this procedure the mass was compacted using Bepex Pharmapactor L200/50P, compression force approximately 45 kN. The compacted mass was sieved and granules of 0.7–1.7 mm were collected.

The material for the powder portion except stearic acid was sieved and mixed until homogenous in a suitable mixer such as Turbula mixer or Zanchetta container mixer. The granule portion and the powder portion and the stearic acid are mixed until homogenous in a suitable mixer such as Turbula mixer or Zanchetta container mixer. The mass is filled into hard gelatine capsules no 3. Instead of hard gelatine capsules, HPMC capsule shells no. 3 can also be used.

EXAMPLE 2

Determination of the Active Metabolite (II) in Human Plasma by Liquid Chromatography-Tandem Mass Spectrometry Preparation of Calibration Samples The active metabolite (II) is added in 20 µl of phosphate buffer, pH 7.2 to 0.5 ml of analyte-free plasma. The amounts of analyte added are 0.100, 0.250, 0.500, 1.00, 2.50, 3.75, 5.00, 7.50 and 12.5 ng. After being vortexed for 20 seconds and left standing for 10 minutes, the 2500 pg of internal standard (R)-N-[4-(1,4,5,6-tetrahydro-4-ethyl-6-oxo-3-pyridazinyl)phenyl]acetamide is added in 20 µl of phosphate buffer, pH 7.2. The mixture is vortexed for 1 minute and left standing for 15 minutes. The calibration samples are alkalised with 50 µl of 0.1 M sodium hydroxide and vortexed for 20 seconds. The calibration samples are extracted with 5 ml of ethyl acetate:hexane (8:2) by vortexing for 3 minutes. After centrifugation for 7 minutes the organic layer is separated and concentrated at 40° C. using TurboVap evaporator. When the calibration samples are dry, 200 µl of ethyl acetate:hexane (8:2) is added, vortexed for 1 minute and concentrated at 40° C. using TurboVap evaporator. After that 200 µl of methanol-2 mM ammonium acetate (1:1) is added, the calibration samples are vortexed for 1 minute and left standing for 5 minutes. After centrifugation for 7 minutes the supernatant is transferred into an unused conical autosampler vial for liquid chromatographic-tandem mass spectrometric analysis.

Preparation of Samples

The samples are processed as described above but the first buffer addition is analyte-free.

Liquid Chromatography-Tandem Mass Spectrometry

Analyses are performed using a PE Sciex API 300 tandem quadrupole mass spectrometer equipped with a heated nebulizer interface. A Hewlett-Packard HP1090L system is used for HPLC. The column applied is a LiChrosorb RP-18 reversed phase column (250×4 mm ID, 10 µm particles, E. Merck). The mobile phase consists of methanol-2 mM ammonium acetate pH 5, (60:40 v/v). The flow-rate is 1 ml/min. An aliquot of 100 µl of extract is injected into the liquid chromatographic column.

The column eluent is flowed into the mass spectrometer without a split. The discharge needle current is set at 4 kV. Nebulizer gas pressure (nitrogen) of 5 bars is used. The interface heater is set at 500° C. Orifice plate voltage is 25 V. Positive ions are sampled into the quadrupole mass analyser.

Determinations are carried out by using the selected reaction monitoring technique. The first quadrupole filter of the mass spectrometer, Q1, is set to pass the protonated molecules at m/z 246 for active metabolite (II) and m/z 260 for internal standard for collision-induced fragmentation in Q2. The respective product ions, at m/z 204 and m/z 218, are then allowed to pass Q3 for monitoring. A dwell time of 200 ms and a pause time of 100 ms is used. The selected reaction monitoring chromatograms are recorded using a PE Sciex API 300 Data System.

Quantitation and Calculations

Peak area ratios of analyte and its internal standard are plotted against concentrations. Determination of calibration curve equations and concentrations of unknown samples are carried out with the PE Sciex API 300 Data System and the PE Sciex MacQuan 1.4 programme. The limit of quantitation is 0.200 ng/ml. The calibration curve for active metabolite (II) is prepared.

Specificity

Figure 2:
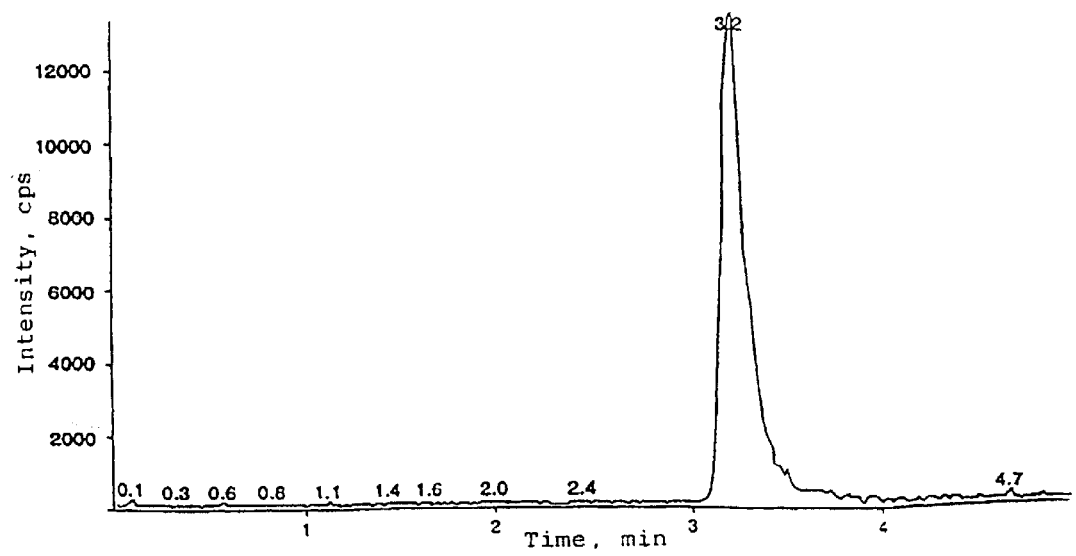
FIG. 2 shows a post-dose plasma sample for the active metabolite (II) from a volunteer as determined by liquid chromatography-tandem mass spectrometry.

The product ions of active metabolite (II) and its internal standard are monitored using the selected reaction monitoring technique. The method is specific regarding the background arising from the plasma. No interfering peaks are observed in blank plasma extracts. FIGS. 1 and 2 show a calibration plasma sample and a post-dose plasma sample from a volunteer.

EXAMPLE 3

In Vitro and In Vivo Experiments for the Compositions of the Invention

Figure 3:
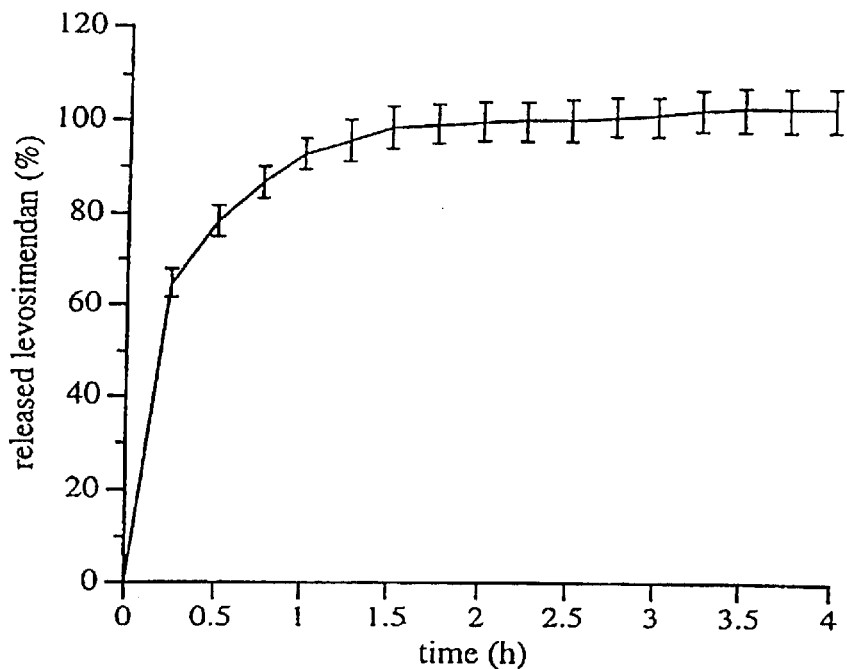
FIG. 3 shows in vitro dissolution curve for formulation 1 of Example 1 in phosphate buffer pH 5.8.
Figure 4:
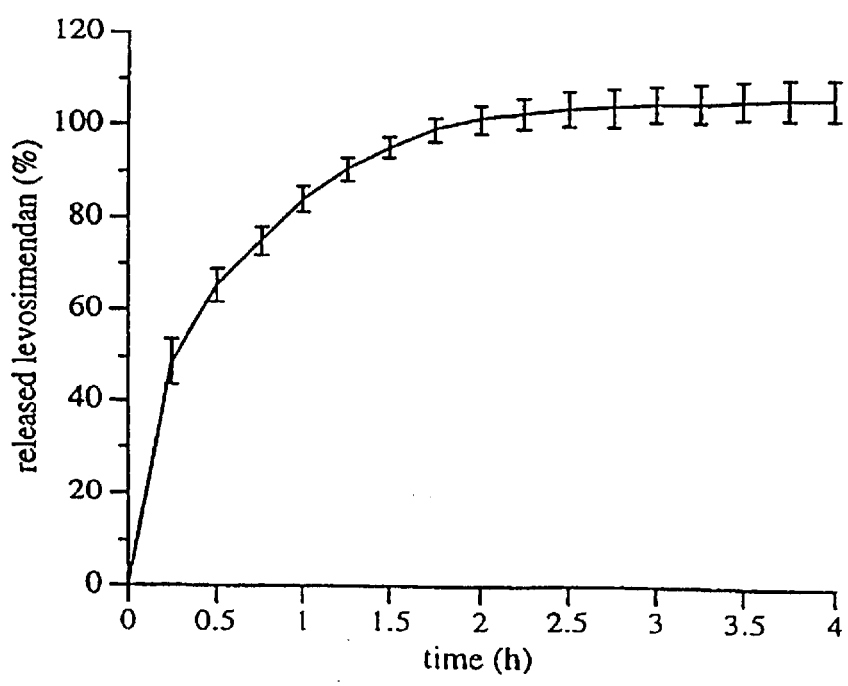
FIG. 4 shows in vitro dissolution curve for formulation 2 of Example 1 in phosphate buffer pH 5.8.
Figure 5:
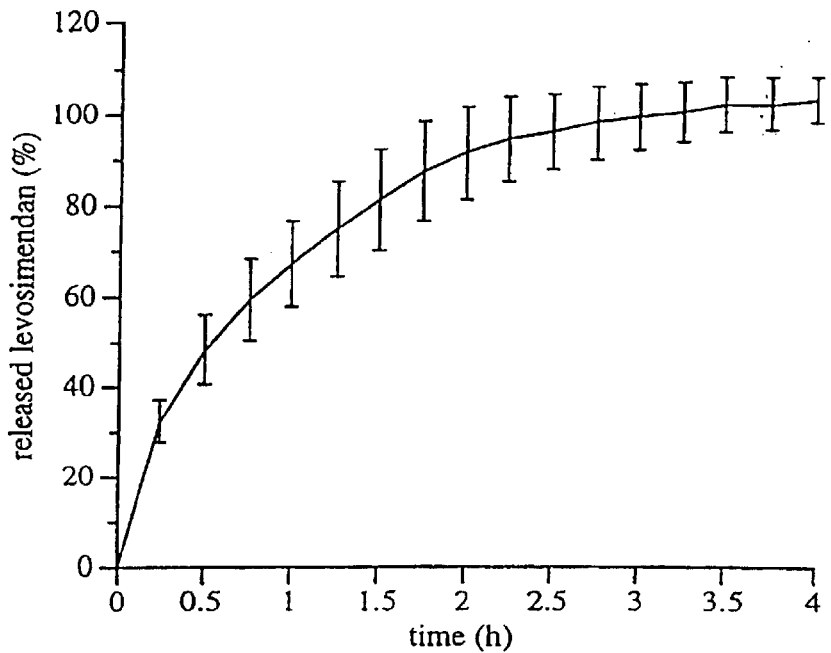
FIG. 5 shows in vitro dissolution curve for formulation 3 of Example 1 in phosphate buffer pH 5.8.

Formulations 1, 2 and 3 of Example 1 were subjected to a dissolution test. The dissolution rate of the formulations was tested by a method of U.S. Pharmacopoeia XXII (basket assembly method) in phosphate buffer pH 5.8 at 50 rpm. The results for formulations 1, 2 and 3 are shown in FIGS. 3, 4 and 5, respectively.

Formulations 1, 2 and 3 of Example 1 were then administered to healthy volunteers as a single oral dose of 2 mg levosimendan. Each group consisted of 9 individuals. The plasma level of metabolite (II) was determined 12 hours after administration. The results are shown in Table 1.

TABLE 1

Plasma concentrations (pg/ml) of metabolite (II) in healthy volunteers 12 h after a single oral dose of levosimendan (n = 9). Clinical study 3001047.

| Subject | Formulation 1 | Formulation 2 | Formulation 3 |
|---|---|---|---|
| 1 | < | < | < |
| 2 | < | 205 | < |
| 3 | 298 | 295 | 347 |
| 4 | 214 | 240 | 262 |
| 5 | < | < | < |
| 6 | 249 | 572 | 1300 |
| 7 | < | < | < |
| 8 | < | < | < |
| 9 | < | 392 | < |
| MEAN | 85 | 189 | 212 |
| SD | 129 | 208 | 429 |

SD = standard deviation
< = under determination limit (200 pg/ml)

EXAMPLE 4

In Vitro and In Vivo Experiments for the Reference Composition

A reference formulation consisting of

| | |
|---|---|
| Levosimendan | 2.0 mg |
| Methocel K4M | 35.0 mg |
| Avicel PH101 | 101.6 mg |
| Stearic acid | 1.4 mg | was subjected to a dissolution test. The formulation was prepared by sieving and mixing the powdery material until homogenous and filling the mass into hard gelatine capsules no 3.

Figure 6:
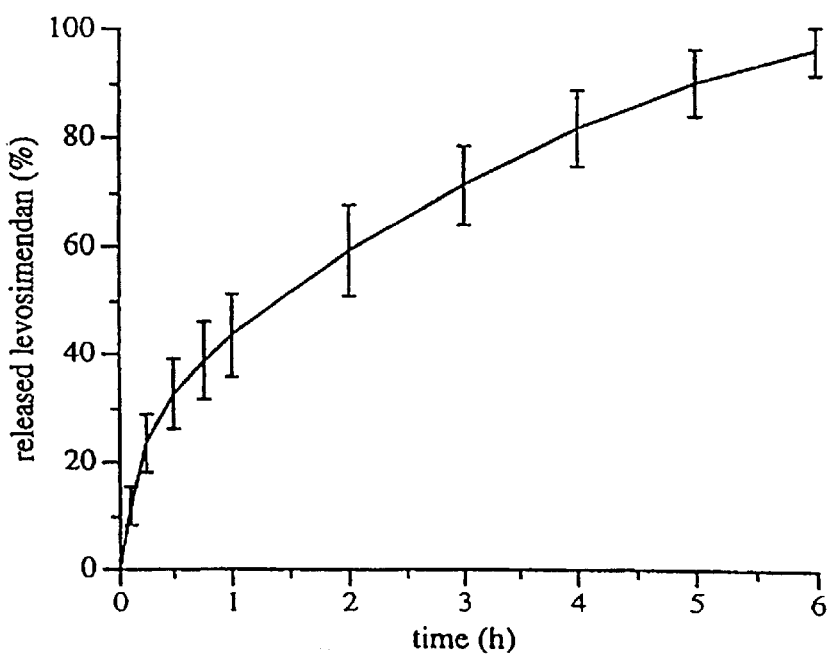
FIG. 6 shows in vitro dissolution curve for the reference formulation of Example 3 in phosphate buffer pH 5.8.

The dissolution rate of the formulations was tested by a method of U.S. Pharmacopoeia XXII (basket assembly method) in phosphate buffer pH 5.8 at 100 rpm. The results are shown in FIG. 6.

The reference formulation was then administered to 8 healthy volunteers as a single oral dose of 2 mg levosimendan. The plasma level of metabolite (II) was determined 12 hours after administration. The results are shown in Table 2.

TABLE 2

Plasma concentration (pg/ml) of metabolite (II) in healthy volunteers 12 h after a single oral dose of levosimendan (n = 8). Clinical study 3001047.

| Subject | Ref. Formulation |
|---|---|
| 1 | < |
| 2 | 283 |
| 3 | 1330 |
| 4 | 1260 |
| 5 | 253 |
| 6 | 268 |
| 7 | 492 |
| 8 | 833 |
| MEAN | 590 |
| SD | 496 |

SD = standard deviation
< = under determination limit (200 pg/ml)

Thus, the formulations of the invention having the total in vitro dissolution time as determined according to the USP XXII basket assembly method in phosphate buffer pH 5.8 substantially between 1 and 4 hours for at least 90 percent of the content of levosimendan give significantly lower plasma level of metabolite (II) in vivo than the reference formulation which have slower dissolution rate.

EXAMPLE 5

Plasma Levels of Levosimendan and the Active Metabolite (II) After 7 Days Levosimendan Administration In a steady-state clinical study 1 mg of levosimendan was administered orally to healthy volunteers three times a day for 7 days. The plasma levels of levosimendan and metabolite (II) were followed during the treatment. The formulation used was as Formulation 3 of Example 1 except that the total amount of levosimendan was 1 mg and of microcrystalline cellulose (Avicel PH-200) 51.0 mg. The mean plasma levels of levosimendan 1 and 4 hours after the last dose (day 7) and of metabolite (II) 8 hours after the last dose (day 7) are shown in Table 3.

TABLE 3

Mean plasma levels of levosimendan and the active metabolite (II) after 7 days levosimendan administration.

| | Levosimendan (day 7) | | Metabolite (II) (day 7) |
|---|---|---|---|
| | 1 h | 4 h | 8 h |
| Plasma level | 15.4 | 8.9 | 3.44 |
| SD (ng/ml) | 8.9 | 4.9 | 1.84 |
| N | 14 | 14 | 13 |

SD = standard deviation
N = number of individuals

The results show that the formulation of the invention provides steady and therapeutically effective plasma levels of levosimendan over an extended period of time while the steady-state plasma levels of metabolite (II) remain at acceptable levels.

EXAMPLE 6

Further Formulation Examples

| Formulation 6 (capsule) | |
|---|---|
| Levosimendan | 1.0 mg |
| Methocel K100LV | 35.0 mg |
| Avicel PH-200 | 80.5 mg |
| Stearic acid | 6.4 mg |

Levosimendan, Methocel K 100 LV and Microcrystalline cellulose (Avicel) were sieved and mixed in a suitable mixer (Turbula or equivalent). Stearic acid was then sieved and mixed with the mass in a suitable mixer (Turbula or equivalent). The mass was then filled into white gelatine capsule shells no 3 using capsule filling machine Harro Höfliger, MG2 or equivalent.

Dissolution data for the above formulation (USP XXII, phosphate buffer, pH 5.8, 100 rpm) is shown in Table 4:

TABLE 4

In vitro dissolution curve for formulation 6 in phosphate buffer pH 5.8, 100 rpm.

| Min | Dissolution % |
|---|---|
| 5 | 12.1 |
| 15 | 43.7 |
| 30 | 65.0 |

TABLE 4-continued

| | |
|---|---|
| 45 | 77.4 |
| 60 | 88.3 |
| 120 | 95.7 |
| 180 | 97.4 |
| 240 | 97.8 |
| 300 | 98.1 |
| 360 | 98.1 |

Formulation 7 (matrix tablet)

| | |
|---|---|
| Levosimendan | 1.0 mg |
| Methocel K100LV | 30.0 mg |
| Croscarmellose sodium | 0.27 mg |
| Avicel PH-200 | 100.0 mg |
| Stearic acid | 4.0 mg |

Levosimendan, Methocel K 100 LV, Croscarmellose sodium and Microcrystalline cellulose (Avicel) were mixed in a suitable mixer (Turbula or equivalent). The powder blend from step was then sieved and mixed in a suitable mixer (Turbula or equivalent). Stearic acid was then sieved and mixed with the powder blend in a suitable mixer (Turbula or equivalent). The mass was then compressed into tablets with a suitable tablet machine (punch diameter 7 mm and concavity radius 10.5 mm, hardness 60 N).

Dissolution data for the above formulation (USP XXII, phosphate buffer, pH 5.8, 100 rpm) is as follows:

TABLE 5

In vitro dissolution curve for formulation 7 in phosphate buffer pH 5.8, 100 rpm.

| Min | Dissolution % |
|---|---|
| 10 | 33.7 |
| 20 | 47.8 |
| 30 | 60.9 |
| 40 | 72.6 |
| 50 | 78.5 |
| 60 | 82.5 |
| 90 | 88.5 |
| 120 | 90.0 |
| 180 | 92.2 |
| 240 | 94.8 |
| 300 | 96.9 |

Formulation 8 (matrix tablet)

| | |
|---|---|
| Levosimendan | 1.0 mg |
| Croscarmellose sodium | 0.11 mg |
| Akofine NF | 10.0 mg |
| Avicel PH-200 | 100.0 mg |

Levosimendan, Croscarmellose sodium and Microcrystalline cellulose (Avicel) were mixed in a suitable mixer (Turbula or equivalent). The powder blend from step was then sieved and mixed in a suitable mixer (Turbula or equivalent). Akofine NF (hydrogenated vegetable oil) was then sieved and mixed with the powder blend in a suitable mixer (Turbula or equivalent). The mass was then compressed into tablets with a suitable tablet machine (punch diameter 7 mm and concavity radius 10.5 mm, hardness 60 N).

Various modifications and variations can be made to the disclosed embodiments without departing from the subject of the invention as defined in the following claims.

What is claimed is:

1. A controlled release composition for oral administration comprising a) a therapeutically effective amount of levosimendan and b) a drug release controlling component for providing the release of levosimendan over an extended period of time and a steady-state plasma level for the levosimendan metabolite (R)-N-[4-(1,4,5,6-tetrahydro-4-methyl-6-oxo-3-pyridazinyl)phenyl]acetamide of less than 20 ng/ml.

2. A composition of claim 1, wherein the drug release controlling component allows levosimendan to be released substantially completely before the composition reaches the large intestine of the host to which the composition is to be administered.

3. A composition of claim 1, wherein the drug release controlling component is hydrophilic gel forming polymer or a vegetable fat or oil or a fatty acid ester.

4. A controlled release composition for oral administration comprising a) a therapeutically effective amount of levosimendan and b) a drug release controlling component for providing the release of levosimendan over an extended period of time, wherein the total in vitro dissolution time of the composition, determined according to the USP XXII basket assembly method in phosphate buffer pH 5.8, ranges from about 1 to about 4 hours for at least 90 percent of the content of levosimendan.

5. A controlled release composition for oral administration comprising (a) a rapid release portion comprising levosimendan optionally together with at least one excipient, and (b) a controlled release portion comprising levosimendan and a drug release controlling component.

6. A composition of claim 5 comprising (a) a rapid release portion in the form of a powder comprising levosimendan together with at least one excipient, and (b) a controlled release portion in the form of granulates comprising levosimendan and a release controlling hydrophilic gel forming polymer.

7. A composition of claim 5, wherein the rapid release portion comprises levosimendan and microcrystalline cellulose.

8. A composition of claim 6, wherein the release controlling hydrophilic gel forming polymer is hydroxypropylmethylcellulose, alginic acid or a mixture thereof.

9. A composition of claim 5, wherein about 25 to about 75% by weight of levosimendan is in the controlled release portion.

10. A composition of claim 6, wherein the amount of the hydrophilic gel forming polymer is about 20 to about 80% by weight of the composition.

11. A composition of claim 1, wherein the drug release controlling component provides for a steady-state plasma level for the levosimendan metabolite of less than 10 ng/ml.

12. A composition of claim 5, wherein about 30 to about 70% by weight of levosimendan is in the controlled release portion.

13. A composition of claim 5, wherein about 40 to about 60% by weight of levosimendan is in the controlled release portion.

14. A composition of claim 6, wherein the amount of the hydrophilic gel forming polymer is about 30 to about 70% by weight of the composition.

15. A method for the treatment of congestive heart failure, which comprises administering to a host in need of the treatment a composition of claim 1.

16. A method for the treatment of congestive heart failure, which comprises administering to a host in need of the treatment a composition of claim 4.

17. A method for the treatment of congestive heart failure, which comprises administering to a host in need of the treatment a composition of claim 5.

* * * * *